(12) United States Patent
Chadeayne

(10) Patent No.: US 11,981,637 B2
(45) Date of Patent: May 14, 2024

(54) 4-PIVALOYLOXY-N-METHYL-TRYPTAMMONIUM CHLORIDE

(71) Applicant: CAAMTECH, INC., Issaquah, WA (US)

(72) Inventor: Andrew R. Chadeayne, Issaquah, WA (US)

(73) Assignee: CAAMTECH, INC., Issaquah, VA (US)

( * ) Notice: Subject to any disclaimer, the term of this patent is extended or adjusted under 35 U.S.C. 154(b) by 0 days.

(21) Appl. No.: 18/051,228

(22) Filed: Oct. 31, 2022

(65) Prior Publication Data
US 2023/0406823 A1 Dec. 21, 2023

Related U.S. Application Data

(60) Provisional application No. 63/350,576, filed on Jun. 9, 2022.

(51) Int. Cl.
*C07D 209/16* (2006.01)
*A61K 45/06* (2006.01)

(52) U.S. Cl.
CPC ............ *C07D 209/16* (2013.01); *A61K 45/06* (2013.01); *C07B 2200/13* (2013.01)

(58) Field of Classification Search
CPC .................................................. C07D 209/16
See application file for complete search history.

(56) References Cited

U.S. PATENT DOCUMENTS

| 2018/0221396 A1 | 8/2018 | Chadeayne |
| 2019/0142851 A1 | 5/2019 | Chadeayne |

FOREIGN PATENT DOCUMENTS

| WO | 2022081549 A1 | 4/2022 |
| WO | WO2022081549 | * 4/2022 |

OTHER PUBLICATIONS

International Search Report dated Jul. 18, 2023 issued in PCT Application No. PCT/US2023/068021.
Dolomanov, O. V., Bourhis, L. J., Gildea, R. J., Howard, J. A. K. & Puschmann, H. (2009). J. Appl. Cryst. 42, 339-341.
Sheldrick, G. M. (2015). Acta Cryst. C71, 3-8.

* cited by examiner

*Primary Examiner* — Rei Tsang Shiao
(74) *Attorney, Agent, or Firm* — RAPHAEL BELLUM PLLC

(57) ABSTRACT

The disclosure relates to (2-{4-[(2,2-dimethylpropanoyl)oxy]-1H-indol-3-yl}ethyl)(methyl)azanium chloride (4-pivaloyloxy-N-methyltryptammonium chloride), crystalline 4-pivaloyloxy-N-methyltryptammonium chloride, and specific crystalline forms thereof, including crystalline form 1 of 4-pivaloyloxy-N-methyltryptammonium chloride, to compositions containing the same, and to methods of treatment using them.

18 Claims, 3 Drawing Sheets

# 4-PIVALOYLOXY-N-METHYL-TRYPTAMMONIUM CHLORIDE

CROSS REFERENCE TO RELATED APPLICATIONS

This application claims priority to U.S. Application No. 63/350,576, filed on Jun. 9, 2022, the disclosure of which is incorporated by reference.

TECHNICAL FIELD

This disclosure relates to (2-{4-[(2,2-dimethylpropanoyl)oxy]-1H-indol-3-yl}ethyl)(methyl)azanium chloride (4-pivaloyloxy-N-methyltryptammonium chloride or 4-PivO-NMT chloride), crystalline 4-PivO-NMT chloride, and specific crystalline forms thereof, including crystalline form 1 of 4-PivO-NMT chloride; to pharmaceutical compositions containing 4-PivO-NMT chloride or crystalline 4-PivO-NMT chloride, including crystalline form 1 of 4-PivO-NMT chloride; and to methods of treatment/therapeutic uses of 4-PivO-NMT chloride or crystalline 4-PivO-NMT chloride, including crystalline form 1 of 4-PivO-NMT chloride.

BACKGROUND OF THE INVENTION

Obtaining specific salts or crystalline forms of an active pharmaceutical ingredient (API) is extremely useful in drug development. It permits better characterization of the drug candidate's chemical and physical properties. Crystalline forms often have better chemical and physical properties than the API in its amorphous state. Such crystalline forms may possess more favorable pharmaceutical and pharmacological properties or be easier to process. Additionally, preparing a crystalline API and solving its crystal structure provides the gold standard for chemical characterization and determining the molecular formula (and molecular weight) of the API. Accordingly, preparing a crystalline form with an accompanying crystal structure thereof prevents potential ambiguities and/or inaccuracies in the API's molecular weight. This is important because the API's molecular weight is used to calculate the concentration of compositions comprising that API. Thus, inaccuracies in molecular weight may lead to errors in the calculations pertaining to dosing, potency, toxicity, etc. in all downstream in vitro and in vivo assays that correlated the concentration of the API with a measured property. Accordingly, there remains a need to obtain and characterize crystalline forms of APIs, such as tryptamines and other psychedelic drug compounds.

SUMMARY OF THE INVENTION

This disclosure relates to (2-{4-[(2,2-dimethylpropanoyl)oxy]-1H-indol-3-yl}ethyl)(methyl)azanium chloride (4-pivaloyloxy-N-methyltryptammonium chloride or 4-PivO-NMT chloride), crystalline 4-PivO-NMT chloride, and specific crystalline forms thereof. In one embodiment, this disclosure pertains to particular crystalline forms of 4-PivO-NMT chloride, including crystalline form 1 of 4-PivO-NMT chloride. In one embodiment, crystalline form 1 of 4-PivO-NMT chloride is characterized by at least one of: an orthorhombic, Pbca space group at a temperature of about 279(2) K; unit cell dimensions a=17.6586(11) Å, b=9.3207(7) Å, c=20.3054(15) Å, α=900, β=90°, and γ=90°; an X-ray powder diffraction (XRPD) pattern substantially similar to FIG. 3; and an X-ray powder diffraction pattern characterized by at least two peaks selected from 8.7, 11.6, and 13.8° 2θ±0.2° 2θ.

The disclosure further relates to a composition comprising 4-PivO-NMT chloride, crystalline 4-PivO-NMT chloride, or specific crystalline forms thereof, such as crystalline form 1 of 4-PivO-NMT chloride, and at least one excipient.

The disclosure also provides a composition comprising 4-PivO-NMT chloride, crystalline 4-PivO-NMT chloride, or specific crystalline forms thereof, such as crystalline form 1 of 4-PivO-NMT chloride, as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone; and at least one excipient.

The disclosure also relates to a method of preventing or treating a psychological disorder comprising the step of administering to a subject in need thereof a therapeutically effective amount of 4-PivO-NMT chloride, crystalline 4-PivO-NMT chloride, or specific crystalline forms thereof, such as crystalline form 1 of 4-PivO-NMT chloride, or a composition according to this disclosure.

The disclosure further relates to a method of preventing or treating inflammation and/or pain, preventing or treating a neurological disorder, modulating activity of a mitogen-activated protein kinase (MAPK), modulating neurogenesis, or modulating neurite outgrowth comprising the step of administering to a subject in need thereof a therapeutically effective amount of a compound of 4-PivO-NMT chloride, crystalline 4-PivO-NMT chloride, or specific crystalline forms thereof, such as crystalline form 1 of 4-PivO-NMT chloride, and to administering a pharmaceutical composition or a composition according to the invention.

As used herein, the term "a subject in need thereof" refers to a person requiring a composition to treat a particular disease or condition (e.g., inflammation, pain, a psychological disorder, modulating activity at a receptor, etc.). In one embodiment, the "subject in need thereof" may be identified by analyzing, diagnosing, and/or determining whether the person (or subject) requires the composition for treatment of a particular disease or condition. In one embodiment, identifying a person in need of treatment comprises diagnosing a person with a medical condition, e.g., a neurological disorder, a chemical imbalance, a hereditary condition, etc. In one embodiment, identifying a person in need of treatment comprises performing a psychiatric evaluation. In one embodiment, identifying a person in need of treatment comprises performing a blood test. In one embodiment, identifying a person in need of treatment comprises determining whether a person has a compulsive disorder. In one embodiment, identifying a person in need of treatment comprises self-identifying as having a compulsive disorder.

DETAILED DESCRIPTION

Compounds

Figure 1:
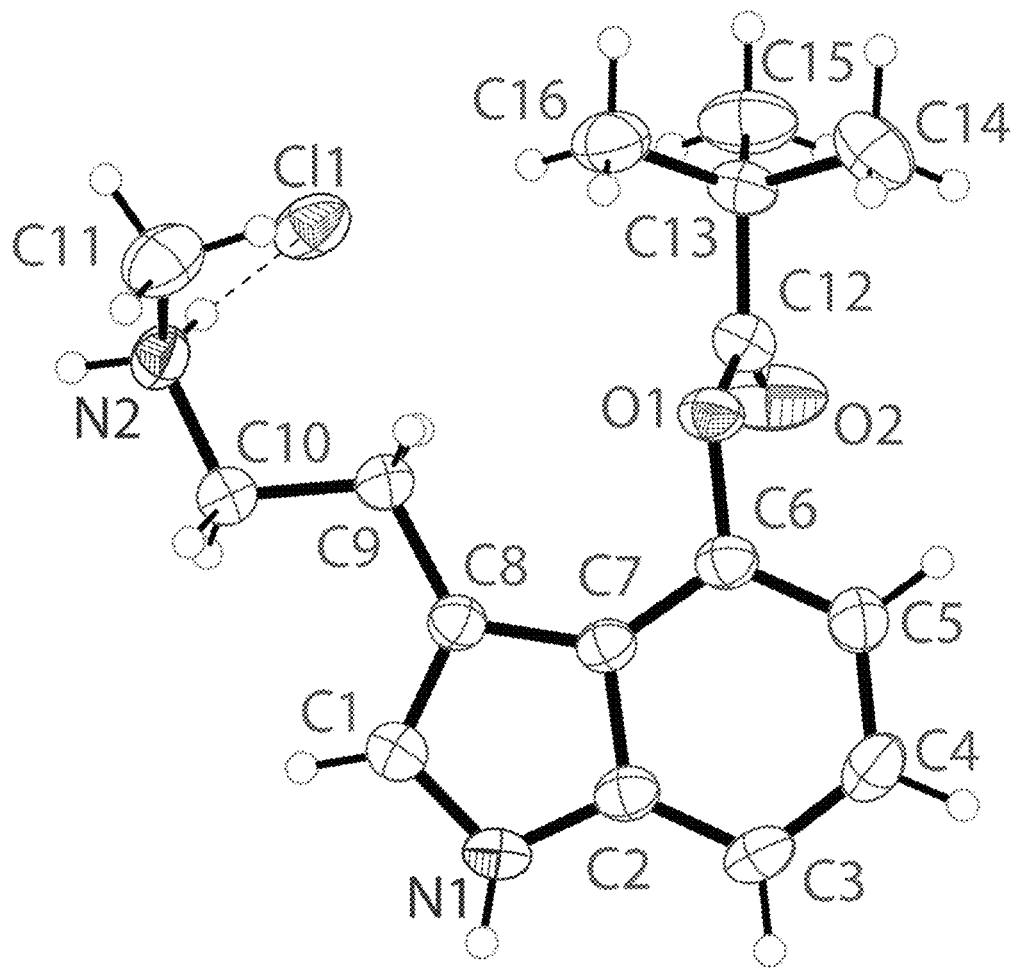
FIG. 1 shows the molecular structure of crystalline form 1 of 4-pivaloyloxy-N-methyltryptammonium chloride.

This disclosure relates to (2-{4-[(2,2-dimethylpropanoyl)oxy]-1H-indol-3-yl}ethyl)(methyl)azanium chloride (4-pivaloyloxy-N-methyltryptammonium chloride or 4-PivO-NMT chloride), crystalline 4-PivO-NMT chloride, and specific crystalline forms thereof, including crystalline form 1 of 4-PivO-NMT chloride, and to compositions containing 4-PivO-NMT chloride or crystalline 4-PivO-NMT chloride (such as crystalline form 1 of 4-PivO-NMT chloride) according to the disclosure. The therapeutic uses of 4-PivO-NMT chloride or crystalline 4-PivO-NMT chloride, including crystalline form 1 of 4-PivO-NMT chloride, according to the disclosure are described below as well as compositions containing it. 4-PivO-NMT chloride or crystalline 4-PivO-NMT chloride, including crystalline form 1 of 4-PivO-NMT chloride, and some exemplary methods used to characterize it are described below.

4-PivO-NMT chloride has the following chemical formula:

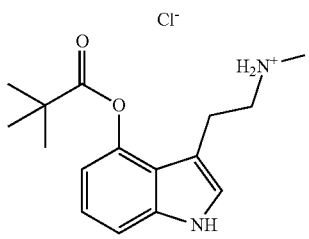 [SMILES: [Cl-] ; C[NH2+]CCc1c[nH]c2cccc(OC(=O)C(C)(C)C)c12]

Methods of Treatment and Therapeutic Uses

4-PivO-NMT chloride or crystalline 4-PivO-NMT chloride (such as crystalline form 1 of 4-PivO-NMT chloride) according to the disclosure, and the methods and the compositions (e.g., pharmaceutical compositions) are used to regulate the activity of a neurotransmitter receptor by administering a therapeutically effective dose of 4-PivO-NMT chloride or crystalline 4-PivO-NMT chloride, such as crystalline form 1 of 4-PivO-NMT chloride, of the disclosure. In one embodiment, 4-PivO-NMT chloride or crystalline 4-PivO-NMT chloride, such as crystalline form 1 of 4-PivO-NMT chloride, according to the disclosure, and the methods and the compositions (e.g., pharmaceutical compositions) are used to treat inflammation and/or pain by administering a therapeutically effective dose of 4-PivO-NMT chloride or crystalline 4-PivO-NMT chloride, such as crystalline form 1 of 4-PivO-NMT chloride, of the disclosure.

Methods of the disclosure also relate to the administration of a therapeutically effective amount of 4-PivO-NMT chloride or crystalline 4-PivO-NMT chloride, such as crystalline form 1 of 4-PivO-NMT chloride, to prevent or treat a disease or condition, such as those discussed below for a subject in need of treatment. 4-PivO-NMT chloride or crystalline 4-PivO-NMT chloride, such as crystalline form 1 of 4-PivO-NMT chloride, may be administered neat or as a composition comprising 4-PivO-NMT chloride or crystalline 4-PivO-NMT chloride, such as crystalline form 1 of 4-PivO-NMT chloride, as discussed below.

4-PivO-NMT chloride or crystalline 4-PivO-NMT chloride, such as crystalline form 1 of 4-PivO-NMT chloride, of the disclosure may be used to prevent and/or treat a psychological disorder. The disclosure provides a method for preventing and/or treating a psychological disorder by administering to a subject in need thereof a therapeutically effective amount of 4-PivO-NMT chloride or crystalline 4-PivO-NMT chloride, such as crystalline form 1 of 4-PivO-NMT chloride, of the disclosure, including the exemplary embodiments discussed herein. The psychological disorder may be chosen from: depression; psychotic disorder; schizophrenia; schizophreniform disorder (acute schizophrenic episode); schizoaffective disorder; bipolar I disorder (mania, manic disorder, manic-depressive psychosis); bipolar II disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome; post-traumatic stress disorder (PTSD); premenstrual dysphoric disorder (PMDD); and premenstrual syndrome (PMS).

4-PivO-NMT chloride or crystalline 4-PivO-NMT chloride, such as crystalline form 1 of 4-PivO-NMT chloride, of the disclosure may be used to prevent and/or treat a brain disorder. The disclosure provides a method for preventing and/or treating a brain disorder (e.g., Huntington's disease, Alzheimer's disease, dementia, and Parkinson's disease) by administering to a subject in need thereof a therapeutically effective amount of 4-PivO-NMT chloride or crystalline 4-PivO-NMT chloride, such as crystalline form 1 of 4-PivO-NMT chloride.

4-PivO-NMT chloride or crystalline 4-PivO-NMT chloride, such as crystalline form 1 of 4-PivO-NMT chloride, of the disclosure may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of 4-PivO-NMT chloride or crystalline 4-PivO-NMT chloride, such as crystalline form 1 of 4-PivO-NMT chloride, including the exemplary embodiments discussed above.

4-PivO-NMT chloride or crystalline 4-PivO-NMT chloride, such as crystalline form 1 of 4-PivO-NMT chloride, of the disclosure may be used to prevent and/or treat inflammation and/or pain, such as for example inflammation and/or pain associated with inflammatory skeletal or muscular diseases or conditions. The disclosure provides a method for preventing and/or treating an inflammation and/or pain by administering to a subject in need thereof a therapeutically effective amount of 4-PivO-NMT chloride or crystalline 4-PivO-NMT chloride, such as crystalline form 1 of 4-PivO-NMT chloride, of the disclosure, including the exemplary embodiments discussed herein. Generally speaking, treatable "pain" includes nociceptive, neuropathic, and mix-type. A method of the disclosure may reduce or alleviate the symptoms associated with inflammation, including but not limited to treating localized manifestation of inflammation characterized by acute or chronic swelling, pain, redness, increased temperature, or loss of function in some cases. A method of the disclosure may reduce or alleviate the symptoms of pain regardless of the cause of the pain, including but not limited to reducing pain of varying severity, i.e., mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include but are not limited to musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

4-PivO-NMT chloride or crystalline 4-PivO-NMT chloride, such as crystalline form 1 of 4-PivO-NMT chloride, of the disclosure may be used to modulate activity of a mitogen-activated protein kinase (MAPK), comprising administering a composition of the invention. MAPKs provide a wide-ranging signaling cascade that allow cells to quickly respond to biotic and abiotic stimuli. Exemplary MAPKs include, but are not limited to, Tropomyosin Receptor Kinase A (TrkA), P38-alpha, and c-Jun N-Terminal Kinase 3 (JNK3). TrkA is a high affinity catalytic receptor of nerve growth factor (NGF) protein. TrkA regulates NGF response, influencing neuronal differentiation and outgrowth as well as programmed cell death. p38-alpha is involved with the regulation of pro-inflammatory cytokines, including TNF-a. In the central nervous system, p38-alpha regulates neuronal death and neurite degeneration, and it is a common target of Alzheimer's disease therapies. JNK3 is a neuronal-specific protein isoform of the JNKs. It is involved with the regulation of apoptosis. JNK3 also plays a role in modulating the response of cytokines, growth factors, and oxidative stress.

As used herein, the term "modulating activity of a mitogen-activated protein kinase" refers to changing, manipulating, and/or adjusting the activity of a mitogen activating protein. In one embodiment, modulating the activity of a MAPK can influence neural health, neurogenesis, neural growth and differentiation, and neurodegenerative diseases.

4-PivO-NMT chloride or crystalline 4-PivO-NMT chloride, such as crystalline form 1 of 4-PivO-NMT chloride, of the disclosure may be used to modulate neurogenesis, comprising administering a composition of the invention. As used herein, the term "modulating neurogenesis" refers to changing, manipulating, and/or adjusting the growth and development of neural tissue. In one embodiment, neurogenesis comprises adult neurogenesis, in which new neural stem cells are generated from neural stem cells in an adult animal. In one embodiment, modulating neurogenesis comprises increasing and/or enhancing the rate at which new neural tissue is developed.

4-PivO-NMT chloride or crystalline 4-PivO-NMT chloride, such as crystalline form 1 of 4-PivO-NMT chloride, of the disclosure may be used to modulate neurite outgrowth, comprising administering a composition of the invention. As used herein, the term "modulating neurite outgrowth" refers to changing, manipulating, and/or adjusting the growth and development of neural projections, or "neurites." In one embodiment, neurogenesis comprises modulating the growth of new neurites, the number of neurites per neuron, and/or neurite length. In one embodiment, modulating neurite outgrowth comprises increasing and/or enhancing the rate and/or length at which neurites develop.

4-PivO-NMT chloride or crystalline 4-PivO-NMT chloride, such as crystalline form 1 of 4-PivO-NMT chloride, of the disclosure may be used to prevent and/or treat sexual health disorders including, but not limited to, hypoactive sexual desire disorder, hyperactive sexual desire disorder, orgasmic disorder, arousal disorder, vaginismus, and dyspareunia. In some embodiments, the disorder is a male sexual dysfunction disorder. In some embodiments, the disorder is a female sexual dysfunction disorder.

4-PivO-NMT chloride or crystalline 4-PivO-NMT chloride, such as crystalline form 1 of 4-PivO-NMT chloride, of the disclosure may be used to prevent and/or treat women's health disorders including, but not limited to, menstrual cramping, dysmenorrhea, post-hysterectomy pain, vaginal or vulvar vestibule mucosa disorder, menopausal-related disorders, vaginal atrophy, or vulvar vestibulitis.

Compositions

The disclosure also relates to compositions comprising an effective amount of 4-PivO-NMT chloride or crystalline 4-PivO-NMT chloride, such as crystalline form 1 of 4-PivO-NMT chloride, and an excipient (e.g., a pharmaceutically-acceptable excipient). In another embodiment, the disclosure also relates to pharmaceutical compositions comprising a therapeutically effective amount of 4-PivO-NMT chloride or crystalline 4-PivO-NMT chloride, such as crystalline form 1 of 4-PivO-NMT chloride, and a pharmaceutically acceptable excipient (also known as a pharmaceutically acceptable carrier). As discussed above, 4-PivO-NMT chloride or crystalline 4-PivO-NMT chloride, such as crystalline form 1 of 4-PivO-NMT chloride, of the disclosure may be, for example, therapeutically useful to prevent and/or treat the psychological disorders, brain disorders, pain, and inflammation as well as the other disorders described herein.

A composition or a pharmaceutical composition of the disclosure may be in any form which contains 4-PivO-NMT chloride or crystalline 4-PivO-NMT chloride, such as crystalline form 1 of 4-PivO-NMT chloride. The composition may be, for example, a tablet, capsule, liquid suspension, injectable, topical, or transdermal. The compositions generally contain, for example, about 1% to about 99% by weight of 4-PivO-NMT chloride or crystalline 4-PivO-NMT chloride, such as crystalline form 1 of 4-PivO-NMT chloride, of the disclosure and, for example, 99% to 1% by weight of at least one suitable pharmaceutically acceptable excipient. In one embodiment, the composition may be between about 5% and about 75% by weight of 4-PivO-NMT chloride or crystalline 4-PivO-NMT chloride, such as crystalline form 1 of 4-PivO-NMT chloride, of the disclosure, with the rest being at least one suitable pharmaceutically acceptable excipient or at least one other adjuvant, as discussed below.

Published US applications US 2018/0221396 A1 and US 2019/0142851 A1 disclose compositions comprising a combination of a first purified psilocybin derivative with a second purified psilocybin derivative, with one or two purified cannabinoids or with a purified terpene. Various ratios of these components in the composition are also disclosed. The disclosures of US 2018/0221396 A1 and US 2019/0142851 A1 are incorporated herein by reference. According to this disclosure, 4-PivO-NMT chloride or crystalline 4-PivO-NMT chloride, such as crystalline form 1 of 4-PivO-NMT chloride, of the disclosure may be used as the "first purified psilocybin derivative" in the compositions described in US 2018/0221396 A1 and US 2019/0142851 A1. Accordingly, this disclosure provides a composition comprising: a first component comprising 4-PivO-NMT chloride or crystalline 4-PivO-NMT chloride, such as crystalline form 1 of 4-PivO-NMT chloride, of the disclosure; at least one second component selected from at least one of (a) a serotonergic drug, (b) a purified psilocybin derivative, (c) a purified cannabinoid, and (d) a purified terpene; and at least one pharmaceutically-acceptable excipient or at least one other adjuvant. Such a composition may be a pharmaceutical composition wherein the components are present individually in therapeutically effective amounts or by combination in a therapeutically effective amount to treat a disease, disorder, or condition as described herein.

When used in such compositions as a first component comprising 4-PivO-NMT chloride or crystalline 4-PivO-NMT chloride, such as crystalline form 1 of 4-PivO-NMT chloride, of the disclosure with a second component selected from at least one of (a) a serotonergic drug, (b) a purified psilocybin derivative, (c) a purified cannabinoid, and (d) a purified terpene, the compositions represent particular embodiments of the invention. Compositions having as a first component 4-PivO-NMT chloride or crystalline 4-PivO-NMT chloride, such as crystalline form 1 of 4-PivO-NMT chloride, of the disclosure with a second component selected from at least one of (e) an adrenergic drug, (f) a dopaminergic drug, (g) a monoamine oxidase inhibitor, (h) a purified erinacine, and (i) a purified hericenone represent additional particular embodiments of the invention represented by the compositions having 4-PivO-NMT chloride or crystalline 4-PivO-NMT chloride, such as crystalline form 1 of 4-PivO-NMT chloride, according to the disclosure. In some embodiments, the first and second components can be administered at the same time (e.g., together in the same composition), or at separate times over the course of treating a patient in need thereof. Such a composition may be a pharmaceutical composition wherein the components are present individually in therapeutically effective amounts or by combination in a therapeutically effective amount to treat a disease, disorder, or condition as described herein.

Within the context of this disclosure, the term "purified" means separated from other materials, such as plant or fungal material, e.g., protein, chitin, cellulose, or water. In one embodiment, the term "purified" refers to a compound substantially free of other materials. In one embodiment, the term "purified" refers to a compound that is substantially free from a second tryptamine compound. In one embodiment, the term "purified" refers to a compound substantially free from histidine. In one embodiment, the term "purified" refers to a compound substantially free from a biological material, such as mold, fungus, plant matter, or bacteria. In one embodiment, the term "purified" refers to a compound substantially free from a paralytic.

In one embodiment, the term "purified" refers to a compound which has been separated from other compounds that are typically co-extracted when the purified compound is extracted from a naturally occurring organism. In one embodiment, a "purified" psilocybin derivative is partially or completely isolated from other psilocybin derivatives present in a source material, such as a psilocybin-containing mushroom. In one example, "purified" baeocystin is substantially free from psilocybin and/or psilocin. By contrast, traditional psilocybin mushroom extracts (aka crude extracts or fruit body extracts) would be expected to contain an unpredictable and varying amount of psilocybin, psilocin, baeocystin, norbaeocystin, salts thereof, or combinations thereof. Other examples of unpurified psilocybin derivatives would include mycelium containing psilocybin derivatives and/or naturally occurring fungal material such as biological material and/or structural material such as chitin. Similarly, the term "cannabis extracts" or "cannabinoid extracts" traditionally refers to whole plants (aka crude or full spectrum extracts) which have not been subjected to further purification to eliminate unwanted molecules that naturally occur in the cannabis plant. For example, a "cannabis extract comprising cannabidiol" could be expected to include cannabidiol (aka "CBD") and also varying amounts of other compounds, including cannabinoids, terpenes, and other biological material.

In one embodiment, the term "purified" refers to a compound or composition that has been crystallized.

In one embodiment, the term "purified" refers to a compound or composition that has been chromatographed, for example by gas chromatography, liquid chromatography (e.g., LC, HPLC, etc.), etc.

In one embodiment, the term "purified" refers to a compound or composition that has been distilled.

In one embodiment, the term "purified" refers to a compound or composition that has been sublimed.

In one embodiment, the term "purified" refers to a compound or composition that has been subject to two or more steps chosen from crystallization, chromatography, distillation, or sublimation.

In one embodiment, the term "purified" refers to a compound that is between 80-100% pure.

In one embodiment, the term "purified" refers to a compound that is between 90-100% pure.

In one embodiment, the term "purified" refers to a compound that is between 95-100% pure.

In one embodiment, the term "purified" refers to a compound that is between 99-100% pure.

In one embodiment, the term "purified" refers to a compound that is between 99.9-100% pure.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments. Exemplary psilocybin derivatives include but are not limited to psilocybin itself and the psilocybin derivatives described in paragraphs [0081]-[0109] of US 2018/0221396 A1 and [0082]-[0110] US 2019/0142851 A1 as well as the disclosed exemplary embodiments. Exemplary cannabinoids include but are not limited to the cannabinoids described in paragraphs [0111]-[0145] of US 2018/0221396 A1 and [0112]-[0146] US 2019/0142851 A1 as well as the disclosed exemplary embodiments. Exemplary terpenes include but are not limited to the terpenes described in paragraphs [0160]-[0238] of US 2018/0221396 A1 and [0161]-[0300] US 2019/0142851 A1 as well as the disclosed exemplary embodiments.

A pharmaceutical formulation of the disclosure may comprise, consist essentially of, or consist of (a) 4-PivO-NMT chloride or crystalline 4-PivO-NMT chloride, such as crystalline form 1 of 4-PivO-NMT chloride, of the disclosure and (b) at least one second active compound selected from a serotonergic drug, a purified psilocybin derivative, a purified cannabinoid, a purified terpene, an adrenergic drug, a dopaminergic drug, a monoamine oxidase inhibitor, a purified erinacine, and a purified hericenone, and (c) a pharmaceutically acceptable excipient. In some embodiments, 4-PivO-NMT chloride or crystalline 4-PivO-NMT chloride, such as crystalline form 1 of 4-PivO-NMT chloride, and the second active compound(s) are each present in a therapeutically effective amount using purposefully engineered and unnaturally occurring molar ratios. Exemplary molar ratios of 4-PivO-NMT chloride or crystalline 4-PivO-NMT chloride, such as crystalline form 1 of 4-PivO-NMT chloride, of the disclosure to the second active compound in a composition of the disclosure include but are not limited to from about 0.1:100 to about 100:0.1, from about 1:100 to about 100:1, from about 1:50 to about 50:1, from about 1:25 to about 25:1, from about 1:20 to about 20:1, from about 1:10 to about 10:1, from about 1:5 to about 5:1, from about 1:2 to about 2:1 or may be about 1:1.

A pharmaceutical formulation of the disclosure may comprise a composition containing 4-PivO-NMT chloride or crystalline 4-PivO-NMT chloride, such as crystalline form 1 of 4-PivO-NMT chloride, of the disclosure and a serotonergic drug, a purified psilocybin derivative, a purified cannabinoid, or a purified terpene, each present in a therapeutically effective amount using purposefully engineered and unnaturally occurring molar ratios. Published US applications US 2018/0221396 A1 and US 2019/0142851 A1 disclose compositions comprising a combination of a purified psilocybin derivative with a second purified psilocybin derivative, with one or two purified cannabinoids or with a purified terpene. According to this disclosure composition containing 4-PivO-NMT chloride or crystalline 4-PivO-NMT chloride, such as crystalline form 1 of 4-PivO-NMT chloride, of the disclosure may be used in place of a "purified psilocybin derivative" in the compositions described in US 2018/0221396 A1 and US 2019/0142851 A1. Accordingly, the disclosure provides a pharmaceutical formulation comprising as (a) 4-PivO-NMT chloride or crystalline 4-PivO-NMT chloride, such as crystalline form 1 of 4-PivO-NMT chloride, of the disclosure and at least one second component selected from (a) a purified psilocybin derivative, (b) a purified cannabinoid, and (c) a purified terpene; and at least one pharmaceutically-acceptable excipient or at least one other adjuvant, as described herein. Such a composition may be a pharmaceutical composition wherein the components are present individually in therapeutic effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments. Some exemplary serotonergic drugs include SSRIs and SNRIs. Some examples of specific serotonergic drugs include the following molecules, including any salts, solvates, or polymorphs thereof: 6-allyl-N,N-diethyl-NL; N,N-dibutyl-T; N,N-diethyl-T; N,N-diisopropyl-T; 5-methyoxy-alpha-methyl-T; N,N-dimethyl-T; 2,alpha-dimethyl-T; alpha,N-dimethyl-T; N,N-dipropyl-T; N-ethyl-N-isopropyl-T; alpha-ethyl-T; 6-N,N-Triethyl-NL; 3,4-dihydro-7-methoxy-1-methyl-C; 7-methyoxy-1-methyl-C; N,N-dibutyl-4-hydroxy-T; N,N-diethyl-4-hydroxy-T; N,N-diisopropyl-4-hydroxy-T; N,N-dimethyl-4-hydroxy-T; N,N-dimethyl-5-hydroxy-T; N,N-dipropyl-4-hydroxy-T; N-ethyl-4-hydroxy-N-methyl-T; 4-hydroxy-N-isopropyl-N-methyl-T; 4-hydroxy-N-methyl-N-propyl-T; 4-hydroxy-N,N-tetramethylene-T; ibogaine; N,N-diethyl-L; N-butyl-N-methyl-T; N,N-diisopropyl-4,5-methylenedioxy-T; N,N-diisopropyl-5,6-methylenedioxy-T; N,N-dimethyl-4,5-methylenedioxy-T; N,N-dimethyl-5,6-methylenedioxy-T; N-isopropyl-N-methyl-5,6-methylenedioxy-T; N,N-diethyl-2-methyl-T; 2-N,N-trimethyl-T; N-acetyl-5-methoxy-T; N,N-diethyl-5-methoxy-T; N,N-diisopropyl-5-methoxy-T; 5-methoxy-N,N-dimethyl-T; N-isopropyl-4-methoxy-N-methyl-T; N-isopropyl-5-methoxy-N-methyl-T; 5,6-dimethoxy-N-isopropyl-N-methyl-T; 5-methoxy-N-methyl-T; 5-methoxy-N,N-tetramethylene-T; 6-methoxy-1-methyl-1,2,3,4-tetrahydro-C; 5-methoxy-2-N,N-trimethyl-T; N,N-dimethyl-5-methylthio-T; N-isopropyl-N-methyl-T; alpha-methyl-T; N-ethyl-T; N-methyl-T; 6-propyl-N-L; N,N-tetramethylene-T; tryptamine; 7-methoxy-1-methyl-1,2,3,4-tetrahydro-C; and alpha,N-dimethyl-5-methoxy-T. For additional information regarding these compounds see Shulgin, A. T., & Shulgin, A. (2016). Tihkal: The Continuation. Berkeley, Calif.: Transform Press. In one embodiment, a serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and/or derivatives thereof. In an exemplary embodiment, the serotonergic drug is 3,4-methylenedioxymethamphetamine.

Exemplary psilocybin derivatives include but are not limited to psilocybin itself and the psilocybin derivatives described in paragraphs [0081]-[0109] of US 2018/0221396 A1 and [0082]-[0110] US 2019/0142851 A1 as well as the disclosed exemplary embodiments, incorporated here by reference.

In one embodiment, the compositions disclosed herein comprise one or more purified psilocybin derivatives chosen from: [3-(2-dimethylaminoethyl)-1H-indol-4-yl] dihydrogen phosphate; 4-hydroxytryptamine; 4-hydroxy-N,N-dimethyltryptamine; [3-(2-methylaminoethyl)-1H-indol-4-yl] dihydrogen phosphate; 4-hydroxy-N-methyltryptamine; [3-(aminoethyl)-1H-indol-4-yl] dihydrogen phosphate; [3-(2-trimethylaminoethyl)-1H-indol-4-yl] dihydrogen phosphate; and 4-hydroxy-N,N,N-trimethyltryptamine.

Exemplary cannabinoids include but are not limited to the cannabinoids described in paragraphs [0111]-[0145] of US 2018/0221396 A1 and [0112]-[0146] US 2019/0142851 A1 as well as the disclosed exemplary embodiments. Examples of cannabinoids within the context of this disclosure include the following molecules: cannabichromene (CBC); cannabichromenic acid (CBCA); cannabichromevarin (CBCV); cannabichromevarinic acid (CBCVA); cannabicyclol (CBL); cannabicyclolic acid (CBLA); cannabicyclovarin (CBLV); cannabidiol (CBD); cannabidiol monomethylether (CBDM); cannabidiolic acid (CBDA); cannabidiorcol (CBD-C1); cannabidivarin (CBDV); cannabidivarinic acid (CBDVA); cannabielsoic acid B (CBEA-B); cannabielsoin (CBE); cannabielsoin acid A (CBEA-A); cannabigerol (CBG); cannabigerol monomethylether (CBGM); cannabigerolic acid (CBGA); cannabigerolic acid monomethylether (CBGAM); cannabigerovarin (CBGV); cannabigerovarinic acid (CBGVA); cannabinodiol (CBND); cannabinodivarin (CBVD); cannabinol (CBN); cannabinol methylether (CBNM); cannabinol-C2 (CBN-C2); cannabinol-C4 (CBN-C4); cannabinolic acid (CBNA); cannabiorcol (CBN-C1); cannabivarin (CBV); cannabitriol (CBT); cannabitriolvarin (CBTV); 10-ethoxy-9-hydroxy-delta-6a-tetrahydrocannabinol; cannbicitran (CBTC); cannabiripsol (CBR); 8,9-dihydroxy-delta-6a-tetrahydrocannabinol; delta-8-tetrahydrocannabinol (Δ8-THC); delta-8-tetrahydrocannabinolic acid (Δ8-THCA); delta-9-tetrahydrocannabinol (THC); delta-9-tetrahydrocannabinol-C4 (THC-C4); delta-9-tetrahydrocannabinolic acid A (THCA-A); delta-9-tetrahydrocannabinolic acid B (THCA-B); delta-9-tetrahydrocannabinolic acid-C4 (THCA-C4); delta-9- tetrahydrocannabiorcol (THC-C1); delta-9-tetrahydrocannabiorcolic acid (THCA-C1); delta-9-tetrahydrocannabivarin (THCV); delta-9-tetrahydrocannabivarinic acid (THCVA); 10-oxo-delta-6a-tetrahydrocannabinol (OTHC); cannabichromanon (CBCF); cannabifuran (CBF); cannabiglendol; delta-9-cis-tetrahydrocannabinol (cis-THC); trihydroxy-delta-9-tetrahydrocannabinol (triOH-THC); dehydrocannabifuran (DCBF); and 3,4,5,6-tetrahydro-7-hydroxy-alpha-alpha-2-trimethyl-9-n-propyl-2,6-metha-no-2H-1-benzoxocin-5-methanol. In one embodiment, the purified cannabinoid is chosen from THC, THCA, THCV, THCVA, CBC, CBCA, CBCV, CBCVA, CBD, CBDA, CBDV, CBVD, CBDVA, CBG, CBGA, CBGV, or CBGVA.

Exemplary terpenes include but are not limited to the terpenes described in paragraphs [0160]-[0238] of US 2018/0221396 A1 and [0161]-[0300] US 2019/0142851 A1 as well as the disclosed exemplary embodiments. In one embodiment, a purified terpene is chosen from acetanisole, acetyl cedrene, anethole, anisole, benzaldehyde, bornyl acetate, borneol, cadinene, cafestol, caffeic acid, camphene, camphor, capsaicin, carene, carotene, carvacrol, carvone, caryophyllene, caryophyllene, caryophyllene oxide, cedrene, cedrene epoxide, cecanal, cedrol, cembrene, cinnamaldehyde, cinnamic acid, citronellal, citronellol, cymene, eicosane, elemene, estragole, ethyl acetate, ethyl cinnamate, ethyl maltol, eucalyptol/1,8-cineole, eudesmol, eugenol, euphol, farnesene, farnesol, fenchone, geraniol, geranyl acetate, guaia-1(10),11-diene, guaiacol, guaiol, guaiene, gurjunene, herniarin, hexanaldehyde, hexanoic acid, humulene, ionone, ipsdienol, isoamyl acetate, isoamyl alcohol, isoamyl formate, isoborneol, isomyrcenol, isoprene, isopulegol, isovaleric acid, lavandulol, limonene, gamma-linolenic acid, linalool, longifolene, lycopene, menthol, methyl butyrate, 3-mercapto-2-methylpentanal, beta-mercaptoethanol, mercaptoacetic acid, methyl salicylate, methylbutenol, methyl-2-methylvalerate, methyl thiobutyrate, myrcene, gamma-muurolene, nepetalactone, nerol, nerolidol, neryl acetate, nonanaldehyde, nonanoic acid, ocimene, octanal, octanoic acid, pentyl butyrate, phellandrene, phenylacetaldehyde, phenylacetic acid, phenylethanethiol, phytol, pinene, propanethiol, pristimerin, pulegone, retinol, rutin, sabinene, squalene, taxadiene, terpineol, terpine-4-ol, terpinolene, thujone, thymol, umbelliferone, undecanal, verdoxan, or vanillin. In one embodiment, a purified terpene is chosen from bornyl acetate, alpha-bisabolol, borneol, camphene, camphor, carene, caryophyllene, cedrene, cymene, elemene, eucalyptol, eudesmol, farnesene, fenchol, geraniol, guaiacol, humulene, isoborneol, limonene, linalool, menthol, myrcene, nerolidol, ocimene, phellandrene, phytol, pinene, pulegone, sabinene, terpineol, terpinolene, or valencene.

As used herein, the term "adrenergic drug" refers to a compound that binds, blocks, or otherwise influences (e.g., via an allosteric reaction) activity at an adrenergic receptor. In one embodiment, an adrenergic drug binds to an adrenergic receptor. In one embodiment, an adrenergic drug indirectly affects an adrenergic receptor, e.g., via interactions affecting the reactivity of other molecules at the adrenergic receptor. In one embodiment, an adrenergic drug is an agonist, e.g., a compound activating an adrenergic receptor. In one embodiment, an adrenergic drug is an antagonist, e.g., a compound binding but not activating an adrenergic receptor, e.g., blocking a receptor. In one embodiment, an adrenergic drug is an effector molecule, e.g., a compound binding to an enzyme for allosteric regulation. In one embodiment, an adrenergic drug acts (either directly or indirectly) at more than one type of receptor (e.g., 5HT, dopamine, adrenergic, acetylcholine, etc.).

In one embodiment, an adrenergic drug is an antidepressant. In one embodiment, an adrenergic drug is a norepinephrine transporter inhibitor. In one embodiment, an adrenergic drug is a vesicular monoamine transporter inhibitor. In one embodiment, an adrenergic drug is chosen from adrenaline, agmatine, amoxapine, aptazapine, atomoxetine, bupropion, clonidine, doxepin, duloxetine, esmirtazpine, mianserin, ketanserin, mirabegron, mirtazapine, norepinephrine, phentolamine, phenylephrine, piperoxan, reserpine, ritodrine, setiptiline, tesofensine, timolol, trazodone, trimipramine, or xylazine.

As used herein, the term "dopaminergic drug" refers to a compound that binds, blocks, or otherwise influences (e.g., via an allosteric reaction) activity at a dopamine receptor. In one embodiment, a dopaminergic drug binds to a dopamine receptor. In one embodiment, a dopaminergic drug indirectly affects a dopamine receptor, e.g., via interactions affecting the reactivity of other molecules at the dopamine receptor. In one embodiment, a dopaminergic drug is an agonist, e.g., a compound activating a dopamine receptor. In one embodiment, a dopaminergic drug is an antagonist, e.g., a compound binding but not activating a dopamine receptor, e.g., blocking a receptor. In one embodiment, a dopaminergic drug is an effector molecule, e.g., a compound binding to an enzyme for allosteric regulation. In one embodiment, a dopaminergic drug acts (either directly or indirectly) at more than one type of receptor (e.g., 5HT, dopamine, adrenergic, acetylcholine, etc.).

In one embodiment, a dopaminergic drug is a dopamine transporter inhibitor. In one embodiment, a dopaminergic drug is a vesicular monoamine transporter inhibitor. In one embodiment, a dopaminergic drug is chosen from aminep-tine, apomorphine, benzylpiperazine, bromocriptine, cabergoline, chlorpromazine, clozapine, dihydrexidine, domperidone, dopamine, fluphenazine, haloperidol, ketamine, loxapine, methamphetamine, olanzapine, pemoline, perphenazine, pergolide, phencyclidine, phenethylamine, phenmetrazine, pimozide, piribedil, a psychostimulant, reserpine, risperidone, ropinirole, tetrabenazine, or thioridazine.

As used herein, the term "monoamine oxidase inhibitor" (MAOI) refers to a compound that blocks the actions of monoamine oxidase enzymes. In one embodiment, a MAOI inhibits the activity of one or both monoamine oxidase A and monoamine oxidase B. In one embodiment a MAOI is a reversible inhibitor of monoamine oxidase A. In one embodiment a MAOI is a drug chosen from isocarboxazid, phenelzine, or tranylcypromine. In one embodiment, a MAOI is β-carboline, pinoline, harmane, harmine, harmaline, harmalol, tetrahydroharmine, 9-methyl-β-carboline, or 3-carboxy-tetrahydrononharman.

In one embodiment, the compositions and methods disclosed herein include one or more purified erinacine molecules. In one embodiment, the compositions and methods disclosed herein comprise purified erinacine A. In one embodiment, the compositions and methods disclosed herein comprise erinacine B. In one embodiment, the compositions and methods disclosed herein comprise erinacine C. In one embodiment, the compositions and methods disclosed herein comprise erinacine D. In one embodiment, the compositions and methods disclosed herein comprise erinacine E. In one embodiment, the compositions and methods disclosed herein comprise erinacine F. In one embodiment, the compositions and methods disclosed herein comprise erinacine G. In one embodiment, the compositions and methods disclosed herein comprise erinacine H. In one embodiment, the compositions and methods disclosed herein comprise erinacine I. In one embodiment, the compositions and methods disclosed herein comprise erinacine J. In one embodiment, the compositions and methods disclosed herein comprise erinacine K In one embodiment, the compositions and methods disclosed herein comprise erinacine P. In one embodiment, the compositions and methods disclosed herein comprise erinacine Q. In one embodiment, the compositions and methods disclosed herein comprise erinacine R. In one embodiment, the compositions and methods disclosed herein comprise erinacine S.

In one embodiment, the compositions and methods disclosed herein include one or more purified hericenone molecules. In one embodiment, the compositions and methods disclosed herein comprise purified hericenone A. In one embodiment, the compositions and methods disclosed herein comprise purified hericenone B. In one embodiment, the compositions and methods disclosed herein comprise purified hericenone C. In one embodiment, the compositions and methods disclosed herein comprise purified hericenone D. In one embodiment, the compositions and methods disclosed herein comprise purified hericenone E. In one embodiment, the compositions and methods disclosed herein comprise purified hericenone F. In one embodiment, the compositions and methods disclosed herein comprise purified hericenone G. In one embodiment, the compositions and methods disclosed herein comprise purified hericenone H.

Exemplary compositions of 4-PivO-NMT chloride or crystalline 4-PivO-NMT chloride, such as crystalline form 1 of 4-PivO-NMT chloride, of the disclosure and a second compound selected from a serotonergic drug, a purified psilocybin derivative, a purified cannabinoid, a purified terpene, an adrenergic drug, a dopaminergic drug, a monoamine oxidase inhibitor, a purified erinacine, and a purified hericenone in exemplary molar ratios are shown in Table 1. 4-PivO-NMT chloride or crystalline 4-PivO-NMT chloride, such as crystalline form 1 of 4-PivO-NMT chloride, of the disclosure may be any one of the exemplary embodiments described above including the crystalline forms as disclosed herein.

TABLE 1

| Second Compound | Molar ratio of 4-PivO-NMT chloride or crystalline 4-PivO-NMT chloride, such as crystalline form 1 of 4-PivO-NMT chloride:second compound | Molar ratio of 4-PivO-NMT chloride or crystalline 4-PivO-NMT chloride, such as crystalline form 1 of 4-PivO-NMT chloride:second compound | Molar ratio of a 4-PivO-NMT chloride or crystalline 4-PivO-NMT chloride, such as crystalline form 1 of 4-PivO-NMT chloride:second compound |
|---|---|---|---|
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| Duloxetine | About 1:100 to about 100:1 | About 1:25 to about 25:1 | About 1:5 to about 5:1 |
| [3-(2-dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |

TABLE 1-continued

| Second Compound | Molar ratio of 4-PivO-NMT chloride or crystalline 4-PivO-NMT chloride, such as crystalline form 1 of 4-PivO-NMT chloride:second compound | Molar ratio of 4-PivO-NMT chloride or crystalline 4-PivO-NMT chloride, such as crystalline form 1 of 4-PivO-NMT chloride:second compound | Molar ratio of a 4-PivO-NMT chloride or crystalline 4-PivO-NMT chloride, such as crystalline form 1 of 4-PivO-NMT chloride:second compound |
|---|---|---|---|
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

Exemplary pharmaceutical compositions of 4-PivO-NMT chloride or crystalline 4-PivO-NMT chloride, such as crystalline form 1 of 4-PivO-NMT chloride, of the disclosure and a second compound selected from a serotonergic drug, a purified psilocybin derivative, a purified cannabinoid, a purified terpene, an adrenergic drug, a dopaminergic drug, a monoamine oxidase inhibitor, a purified erinacine, and a purified hericenone and an excipient with exemplary molar ratios of 4-PivO-NMT chloride or crystalline 4-PivO-NMT chloride, such as crystalline form 1 of 4-PivO-NMT chloride, to the second compound are shown in Table 2. 4-PivO-NMT chloride or crystalline 4-PivO-NMT chloride, such as crystalline form 1 of 4-PivO-NMT chloride, of the disclosure may be any one of the exemplary embodiments described above including the crystalline forms as disclosed herein.

TABLE 2

| Second Compound | Molar ratio of a 4-PivO-NMT chloride or crystalline 4-PivO-NMT chloride, such as crystalline form 1 of 4-PivO-NMT chloride:second compound | Molar ratio of a 4-PivO-NMT chloride or crystalline 4-PivO-NMT chloride, such as crystalline form 1 of 4-PivO-NMT chloride:second compound | Molar ratio of a 4-PivO-NMT chloride or crystalline 4-PivO-NMT chloride, such as crystalline form 1 of 4-PivO-NMT chloride:second compound |
|---|---|---|---|
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| Duloxetine | About 1:100 to about 100:1 | About 1:25 to about 25:1 | About 1:5 to about 5:1 |
| [3-(2-dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |

TABLE 2-continued

| Second Compound | Molar ratio of a 4-PivO-NMT chloride or crystalline 4-PivO-NMT chloride, such as crystalline form 1 of 4-PivO-NMT chloride:second compound | Molar ratio of a 4-PivO-NMT chloride or crystalline 4-PivO-NMT chloride, such as crystalline form 1 of 4-PivO-NMT chloride:second compound | Molar ratio of a 4-PivO-NMT chloride or crystalline 4-PivO-NMT chloride, such as crystalline form 1 of 4-PivO-NMT chloride:second compound |
|---|---|---|---|
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

An "effective amount" or a "therapeutically effective amount" of 4-PivO-NMT chloride or crystalline 4-PivO-NMT chloride, such as crystalline form 1 of 4-PivO-NMT chloride, of the disclosure is generally in the range of about 0.1 to about 100 mg daily (oral dose), of about 0.1 to about 50 mg daily (oral dose), of about 0.25 to about 25 mg daily (oral dose), of about 0.1 to about 5 mg daily (oral dose), or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155(2001), which is incorporated herein by reference. 4-PivO-NMT chloride or crystalline 4-PivO-NMT chloride, such as crystalline form 1 of 4-PivO-NMT chloride, of the disclosure and pharmaceutical compositions containing it may be used in combination with other agents that are generally administered to a patient being treated for psychological and other disorders discussed above. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. Exemplary carriers include those that do not substantially alter the structure or activity of 4-PivO-NMT chloride or crystalline 4-PivO-NMT chloride, such as crystalline form 1 of 4-PivO-NMT chloride, of the disclosure, or produce undesirable biological effects or otherwise interact in a deleterious manner with any other component(s) of the pharmaceutical composition.

The pharmaceutical compositions of the disclosure may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, 4-PivO-NMT chloride or crystalline 4-PivO- NMT chloride, such as crystalline form 1 of 4-PivO-NMT chloride, of the disclosure may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like, (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents. In some embodiments, the excipient is not water. In some embodiments, the excipient is not a solvent (e.g., EtOH, diethyl ether, ethyl acetate, or hydrocarbon-based solvents (e.g., hexanes). In some embodiments, the dosage form is substantially free of water and/or solvents, for example less than about 5% water by mass, less than 2% water by mass, less than 1% water by mass, less than 0.5% water by mass, or less than 0.1% water by mass.

Excipients or pharmaceutically acceptable adjuvants known in the pharmaceutical formulation art may also be used in the pharmaceutical compositions of the disclosure. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the disclosure may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier).

Administration of 4-PivO-NMT chloride or crystalline 4-PivO-NMT chloride, such as crystalline form 1 of 4-PivO-NMT chloride, of the disclosure in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

EXAMPLES

The preparation and characterization of crystalline form 1 of (2-{4-[(2,2-dimethylpropanoyl)oxy]-1H-indol-3-yl}ethyl)(methyl)azanium chloride (4-pivaloyloxy-N-methyltryptammonium chloride or 4-PivO-NMT chloride) is described below.

Single Crystal X-Ray Diffraction (SCXRD) Characterization: Data were collected on a Bruker D8 Venture CMOS Diffractometer equipped with an Oxford Cryosystems Cryostream cooling device and using Mo Kα radiation. Structures were solved using the Bruker SHELXTL program and refined with the SHELXTL program as part of the Bruker SHELXTL suite, or OLEX2 software. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Preparation and Characterization of Crystalline Form 1 of 4-Pivaloyloxy-N-Methyltryptammonium Chloride Synthesis A dry flask under an atmosphere of nitrogen was charged with 8 mL of dichloromethane. 125 mg of norpsilocin was added and the contents were cooled at 0° C. To the resulting solution was added triethylamine (1.2 equiv) followed by di-tert-butyl-dicarbonate (1.1 equiv) in a dropwise manner and the contents were then stirred at room temperature for twelve hours. Extraction was done twice with dichloromethane and cold water followed by brine. The organic layer was dried with sodium sulfate and solvent was removed in vacuo to yield a brown-black oily residue. It was triturated with pentane to yield a tan powder that was filtered and used in the next reaction without further purification.

Under nitrogen to a dry flask containing the above residue was added 10 mL of dichloromethane and the contents were cooled at 0° C. To the resulting solution was added triethylamine (2 equiv) followed by Pivaloyl chloride (1.5 equiv) in a dropwise manner and the contents were then stirred at room temperature for twelve hours. Extraction was done thrice with dichloromethane and cold water followed by brine. The organic layer was then dried with sodium sulfate and solvent was removed in vacuo to yield a red oily residue. The residue was diluted with dichloromethane (12 mL) and to resulting solution at 0° C. was added HCl in ether (2N, 10 equiv) in a dropwise manner and the contents were then stirred at room temperature for 10 hours. The resulting precipitate was filtered and washed with cold DCM, diethyl ether and dried under vacuum to yield the desired compound as yellow solid (42 mg, 27% yield).

$^1$H NMR (400 MHz, Deuterium Oxide): δ 7.46 (dd, J=0.8, 8, 1H, ArH), 7.26 (t, J=8.0 Hz, 2H, ArH), 6.82 (dd, J=0.8, 7.7 Hz, 1H, ArH), 3.39 (t, J=6.3 Hz, 2H, CH$_2$), 3.12 (t, J=6.3 Hz, 2H, CH$_2$), 2.68 (s, 3H, CH$_3$), 1.44 (s, 9H, CH$_3$).

$^{13}$C NMR (101 MHz, Deuterium Oxide): δ 143.60 (ArC), 125.33 (ArC), 122.57 (ArC), 111.88 (ArC), 110.41 (ArC), 107.02 (ArC), 49.52 (C), 39.09 (CH$_2$), 32.79 (CH$_2$), 26.37 (CH$_3$), 22.84 (CH$_3$).

Crystallization

The powder was recrystallized by slow evaporation in acetone to yield single crystals suitable for X-ray analysis.

Single Crystal Characterization

The single crystal data and structure refinement parameters for the crystalline form 1 structure of 4-PivO-NMT chloride are reported in Table 3, below.

FIG. 1 shows the molecular structure of crystalline form 1 of 4-PivO-NMT chloride, showing the atomic labeling.

Figure 2:
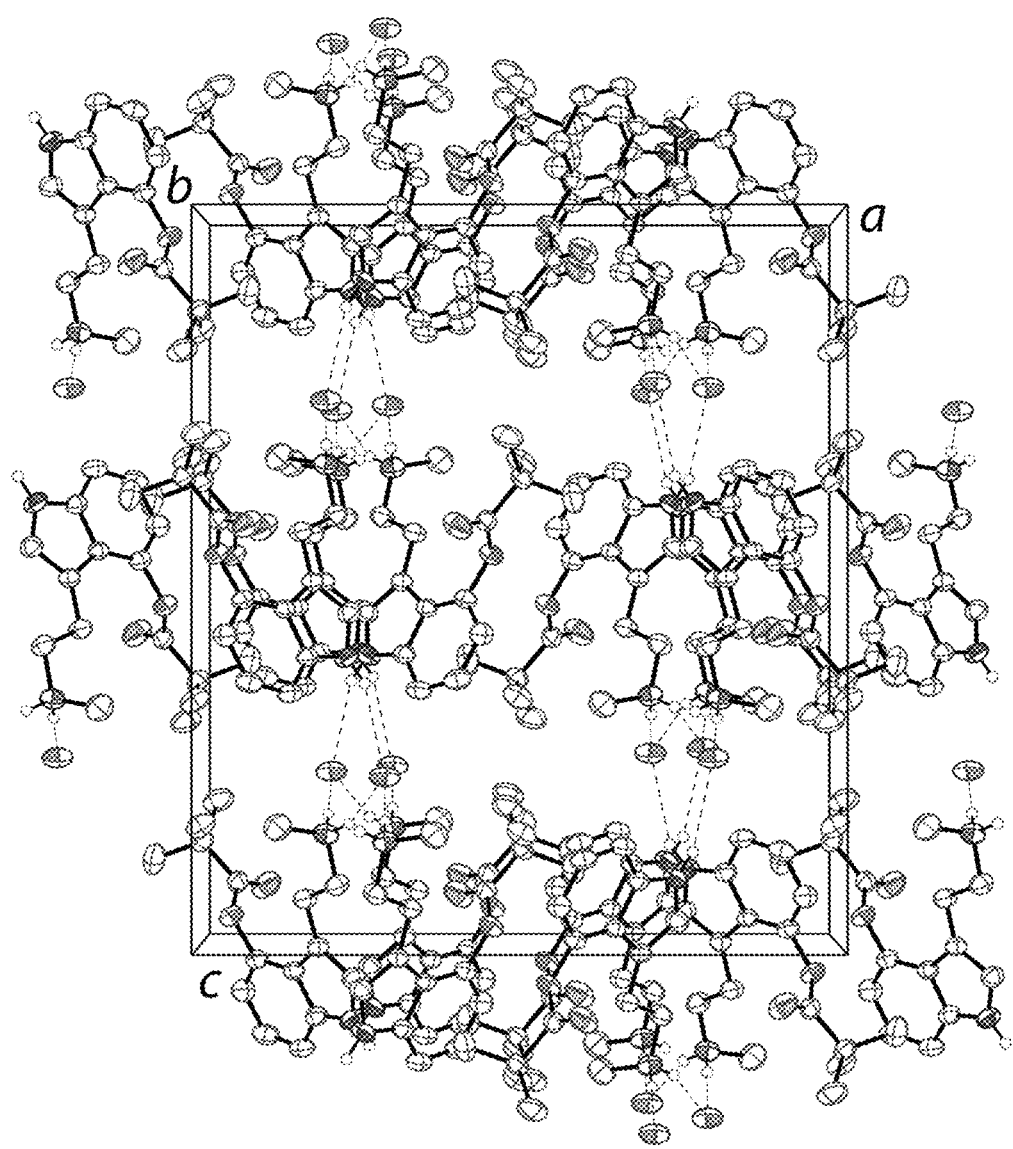
FIG. 2 shows the unit cell of crystalline form 1 of 4-pivaloyloxy-N-methyltryptammonium chloride along the b-axis.

FIG. 2 shows the unit cell of crystalline form 1 of 4-PivO-NMT chloride along the b-axis.

Simulated Powder X-Ray Diffraction (PXRD) Pattern

Figure 3:
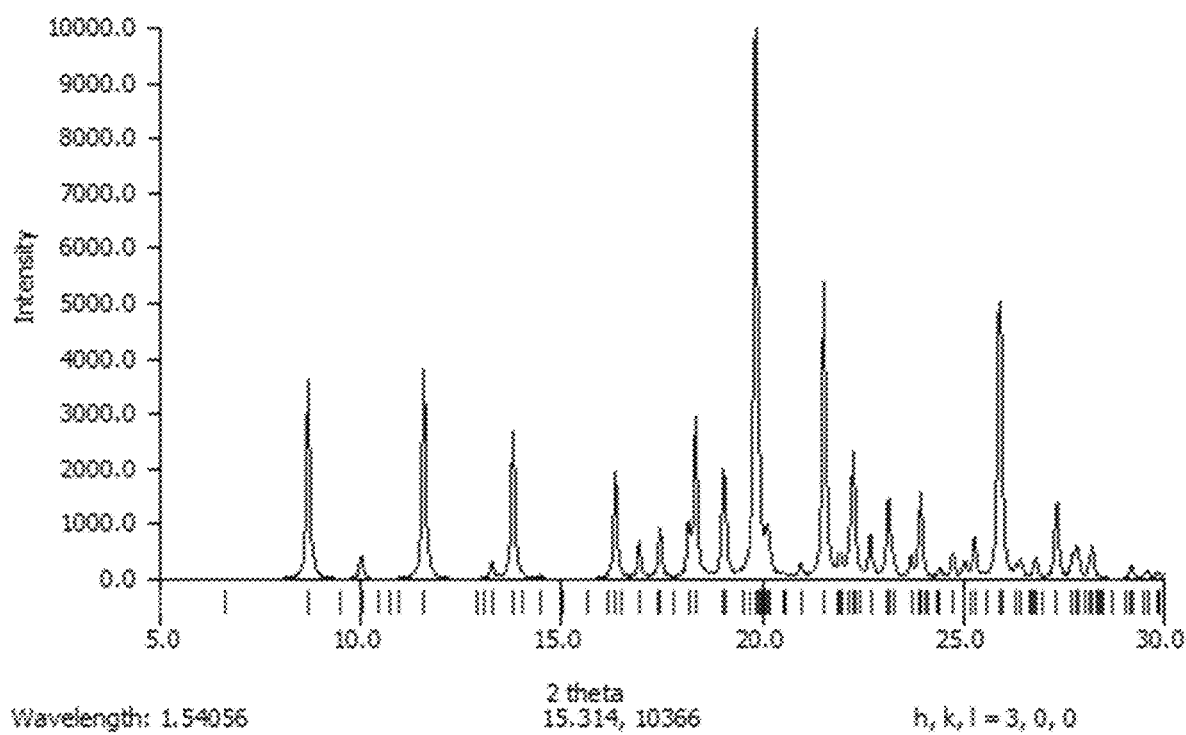
FIG. 3 shows the simulated X-ray powder diffraction pattern (XRPD) for crystalline form 1 of 4-pivaloyloxy-N-methyltryptammonium chloride.

FIG. 3 shows a simulated X-ray powder diffraction pattern (XRPD) for crystalline form 1 of 4-PivO-NMT chloride generated from its single crystal data. Table 4 lists the angles, ° 2θ±0.2° 2θ, and d-spacing of the peaks identified in the experimental XRPD pattern of FIG. 3. The entire list of peaks, or a subset thereof, may be sufficient to characterize the cocrystal. For example, the cocrystal may be characterized by at least two peaks selected from the peaks at 8.7, 11.6, and 13.8° 2θ±0.2° 2θ or their corresponding d-spacing as well as by an XRPD pattern substantially similar to FIG. 3.

TABLE 3

| Crystal data | |
|---|---|
| Chemical formula | Cl•C$_{16}$H$_{23}$N$_2$O$_2$ |
| M$_r$ | 310.81 |
| Crystal system, space group | orthorhombic, Pbca |
| Temperature (K) | 279(2) |
| a, b, c (Å) | 17.6586(11), 9.3207(7), 20.3054(15) |
| α (°) | 90 |
| β (°) | 90 |
| γ (°) | 90 |
| V (Å$^3$) | 3342.1(4) |
| Z | 8 |
| F(000) | 1328 |
| D$_x$ (Mg m$^{-3}$) | 1.235 |
| Radiation type | Mo Kα |
| λ (Å) | 0.71073 |
| θ (°) | 2.67-26.07 |
| μ (mm$^{-1}$) | 0.235 |
| Crystal size (mm) | 0.31 × 0.27 × 0.1 |
| Crystal color | colourless |
| Crystal description | BLOCK |
| Data collection | |
| Diffractometer | Bruker APEX-II CCD |
| Absorption correction | Multi-scan SADABS (Bruker, 2016) was used. wR2(int) was 0.0575 before and 0.0514 after correction. The Ratio of minimum to maximum transmission is 0.9341. The λ/2 correction factor is not present. |
| T$_{min}$, T$_{max}$ | 0.6963, 0.7454 |
| No. of measured, independent, and observed [I > 2σ(I)] reflections | 53783, 3417, 2837 |
| R$_{int}$ | 0.0405 |
| θ$_{max}$, θ$_{min}$ (°) | 26.396, 3.058 |
| h, k, l | −22 → 21, −11 → 11, −25 → 25 |
| Refinement | |
| R[F$^2$ > 2σ(F$^2$)], wR(F$^2$), S | 0.0353, 0.0948, 1.025 |
| No. of reflections | 3417 |
| No. of parameters | 206 |
| No. of restraints | 3 |
| H-atom treatment | H atoms treated by a mixture of independent and constrained refinement |
| w | w = 1/[σ$^2$(F$_o^2$) + (0.0399P)$^2$ + 1.5512P] where P = (F$_o^2$ + 2F$_c^2$)/3 |
| (Δ/σ)$_{max}$ | 0.001 |
| Δρ$_{max}$, Δρ$_{min}$ (e Å$^{-3}$) | 0.255, −0.333 |

Data collection: Bruker APEX32; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009).

TABLE 4

| d-spacing (Å) | °2θ ± 0.2°2θ | Intensity |
|---|---|---|
| 10.15 | 8.70 | 33401 |
| 8.83 | 10.01 | 5003 |
| 8.80 | 10.04 | 376 |
| 7.64 | 11.58 | 62760 |
| 6.66 | 13.28 | 6595 |
| 6.41 | 13.80 | 53484 |
| 6.40 | 13.83 | 11643 |
| 6.11 | 14.48 | 1402 |
| 5.42 | 16.34 | 63941 |
| 5.23 | 16.94 | 23867 |
| 5.09 | 17.40 | 1937 |
| 5.08 | 17.46 | 34661 |
| 4.88 | 18.17 | 36541 |
| 4.83 | 18.34 | 121006 |
| 4.66 | 19.03 | 28986 |
| 4.65 | 19.05 | 63393 |
| 4.54 | 19.53 | 1088 |
| 4.47 | 19.85 | 504152 |
| 4.41 | 20.10 | 18320 |
| 4.40 | 20.16 | 28475 |
| 4.40 | 20.17 | 3747 |
| 4.32 | 20.53 | 1847 |
| 4.24 | 20.96 | 13149 |
| 4.12 | 21.54 | 269504 |
| 4.12 | 21.56 | 49807 |
| 4.05 | 21.94 | 22207 |
| 4.04 | 21.99 | 633 |
| 4.01 | 22.15 | 10396 |
| 3.99 | 22.26 | 134243 |
| 3.98 | 22.32 | 14986 |
| 3.91 | 22.69 | 50817 |
| 3.84 | 23.12 | 21826 |
| 3.84 | 23.15 | 81379 |
| 3.82 | 23.27 | 14765 |
| 3.75 | 23.70 | 26251 |
| 3.71 | 23.94 | 114870 |
| 3.64 | 24.41 | 14317 |
| 3.60 | 24.74 | 36101 |
| 3.55 | 25.04 | 23052 |
| 3.52 | 25.28 | 58542 |
| 3.44 | 25.89 | 159782 |
| 3.44 | 25.90 | 95632 |
| 3.43 | 25.93 | 218412 |
| 3.43 | 25.95 | 16664 |
| 3.38 | 26.31 | 13292 |
| 3.37 | 26.43 | 25887 |
| 3.34 | 26.70 | 361 |
| 3.33 | 26.74 | 2118 |
| 3.32 | 26.80 | 33999 |
| 3.26 | 27.34 | 130774 |
| 3.22 | 27.72 | 32814 |
| 3.20 | 27.81 | 28873 |
| 3.20 | 27.86 | 37137 |
| 3.17 | 28.16 | 12237 |
| 3.16 | 28.22 | 53685 |
| 3.15 | 28.34 | 1057 |
| 3.14 | 28.40 | 1041 |
| 3.14 | 28.43 | 270 |
| 3.13 | 28.49 | 2985 |
| 3.06 | 29.14 | 4217 |
| 3.06 | 29.20 | 25071 |
| 3.03 | 29.50 | 3976 |
| 3.02 | 29.59 | 15988 |
| 2.99 | 29.83 | 14544 |

REFERENCES

Dolomanov, O. V., Bourhis, L. J., Gildea, R. J., Howard, J. A. K. & Puschmann, H. (2009). J. Appl. Cryst. 42, 339-341.

Sheldrick, G. M. (2015). Acta Cryst. C71, 3-8.

The claimed invention is:

1. (2-{4-[(2,2-dimethylpropanoyl)oxy]-1H-indol-3-yl}ethyl)(methyl)azanium chloride (4-pivaloyloxy-N-methyltryptammonium chloride).

2. A crystalline form 1 of (2-{4-[(2,2-dimethylpropanoyl)oxy]-1H-indol-3-yl}ethyl)(methyl)azanium chloride (4-pivaloyloxy-N-methyltryptammonium chloride), characterized by at least one of:
  an orthorhombic crystal system at a temperature of about 297 K;
  a Pbca space group at a temperature of about 297 K;
  unit cell dimensions a=17.6586(11) Å, b=9.3207(7) Å, c=20.3054(15) Å, $\alpha=90°$, $\beta=90°$, and $\gamma=90°$;
  an X-ray powder diffraction pattern substantially similar to FIG. 3; or
  an X-ray powder diffraction pattern characterized by at least two peaks selected from 8.7, 11.6, and 13.8°2θ±0.2°2θ.

3. A composition comprising 4-pivaloyloxy-N-methyltryptammonium chloride according to claim 1 and an excipient.

4. A composition comprising crystalline 4-pivaloyloxy-N-methyltryptammonium chloride according to claim 2 and an excipient.

5. A composition comprising 4-pivaloyloxy-N-methyltryptammonium chloride according to claim 1 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

6. A composition comprising crystalline 4-pivaloyloxy-N-methyltryptammonium chloride according to claim 2 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

7. A method of preventing or treating a psychological disorder comprising the step of:
  administering to a subject in need thereof a therapeutically effective amount of 4-pivaloyloxy-N-methyltryptammonium chloride according to claim 1.

8. A method of preventing or treating a psychological disorder comprising the step of:
  administering to a subject in need thereof a therapeutically effective amount of crystalline 4-pivaloyloxy-N-methyltryptammonium chloride according to claim 2.

9. A method of preventing or treating a psychological disorder comprising the step of:
  administering to a subject in need thereof a composition according to claim 3.

10. A method of preventing or treating a psychological disorder comprising the step of:
  administering to a subject in need thereof a composition according to claim 4.

11. A method of preventing or treating inflammation and/or pain comprising the step of:
  administering to a subject in need thereof a therapeutically effective amount of 4-pivaloyloxy-N-methyltryptammonium chloride according to claim 1.

12. A method of preventing or treating inflammation and/or pain comprising the step of:
  administering to a subject in need thereof a therapeutically effective amount of crystalline 4-pivaloyloxy-N-methyltryptammonium chloride according to claim 2.

13. A method of preventing or treating inflammation and/or pain comprising the step of:

administering to a subject in need thereof a composition according to claim 3.

14. A method of preventing or treating inflammation and/or pain comprising the step of:
administering to a subject in need thereof a composition according to claim 4.

15. A method of preventing or treating a psychological disorder comprising the step of:
administering to a subject in need thereof a composition according to claim 5.

16. A method of preventing or treating a psychological disorder comprising the step of:
administering to a subject in need thereof a composition according to claim 6.

17. A method of preventing or treating inflammation and/or pain comprising the step of:
administering to a subject in need thereof a composition according to claim 5.

18. A method of preventing or treating inflammation and/or pain comprising the step of:
administering to a subject in need thereof a composition according to claim 6.

\* \* \* \* \*